US012708324B2

(12) United States Patent
Peters et al.

(10) Patent No.: US 12,708,324 B2
(45) Date of Patent: Aug. 18, 2026

(54) WEARABLE HEALTH DEVICE SYSTEM WITH AUTOMATIC REFERENCING OF SEISMOCARDIOGRAPHY SIGNALS

(71) Applicant: Robert Bosch GmbH, Stuttgart (DE)

(72) Inventors: Christian Peters, Sunnyvale, CA (US); Thomas Rocznik, Mountain View, CA (US); Seow Yuen Yee, Mountain View, CA (US); Robert Duerichen, Oxford (GB)

(73) Assignee: Robert Bosch GmbH, Stuttgart (DE)

( * ) Notice: Subject to any disclaimer, the term of this patent is extended or adjusted under 35 U.S.C. 154(b) by 1631 days.

(21) Appl. No.: 16/975,078

(22) PCT Filed: Feb. 25, 2019

(86) PCT No.: PCT/EP2019/054551
§ 371 (c)(1),
(2) Date: Aug. 21, 2020

(87) PCT Pub. No.: WO2019/166359
PCT Pub. Date: Sep. 6, 2019

(65) Prior Publication Data

US 2021/0085249 A1 Mar. 25, 2021

Related U.S. Application Data

(60) Provisional application No. 62/635,824, filed on Feb. 27, 2018.

(51) Int. Cl.
*A61B 5/00* (2006.01)
*A61B 5/28* (2021.01)

(52) U.S. Cl.
CPC .............. *A61B 5/6823* (2013.01); *A61B 5/28* (2021.01); *A61B 5/7282* (2013.01); *A61B 2562/0219* (2013.01)

(58) Field of Classification Search
None
See application file for complete search history.

(56) References Cited

U.S. PATENT DOCUMENTS

2001/0004234 A1* 6/2001 Petelenz .............. A61B 5/6838 128/903
2011/0295127 A1 12/2011 Sandler et al.
(Continued)

FOREIGN PATENT DOCUMENTS

CN 101569526 A 11/2009
CN 104349711 A 2/2015
(Continued)

OTHER PUBLICATIONS

Bosch Sensortec, BMA280 Digital, triaxial acceleration sensor, Data Sheet, Aug. 2019. Please note that an electronic copy of this document could not be uploaded to EFS due to password-protected security settings associated with the document, but a secured version of the document is available at https://www.bosch-sensortec.com/media/boschsensortec/downloads/datasheets/bst-bma280-ds000.pdf (last accessed Aug. 21, 2020) (119 pages).
(Continued)

*Primary Examiner* — Erica S Lee
(74) *Attorney, Agent, or Firm* — Maginot, Moore & Beck LLP

(57) ABSTRACT

A wearable health device system includes a housing configured to be worn by a subject, and a sensor assembly with at least two accelerometers which sense acceleration along non-parallel axes. A processor operably connected to the sensor assembly and a memory executes program instructions in the memory to obtain SCG template data from the accelerometers and divide the obtained SCG template data into at least one cardiac cycle segment by converting the SCG template data into polar coordinate SCG template data or spherical coordinate SCG template data. At least one
(Continued)

reference cardiac event is identified in the SCG template data using the converted SCG template data, and the SCG template data is divided into at least one cardiac cycle segment based upon the referenced cardiac event.

18 Claims, 12 Drawing Sheets

(56) References Cited

U.S. PATENT DOCUMENTS

| | | | | |
|---|---|---|---|---|
| 2014/0066798 | A1 | 3/2014 | Albert | |
| 2015/0038856 | A1* | 2/2015 | Houlton | A61B 5/6826 600/484 |
| 2015/0305675 | A1 | 10/2015 | Miller et al. | |
| 2016/0302677 | A1 | 10/2016 | He | |
| 2017/0238847 | A1 | 8/2017 | Inan et al. | |
| 2017/0347899 | A1 | 12/2017 | Bhushan et al. | |
| 2018/0192888 | A1 | 7/2018 | Yee et al. | |

FOREIGN PATENT DOCUMENTS

| | | | |
|---|---|---|---|
| CN | 105453128 | A | 3/2016 |
| CN | 105530866 | A | 4/2016 |
| CN | 106971059 | A | 7/2017 |
| CN | 107072581 | A | 8/2017 |
| CN | 107106054 | A | 8/2017 |
| CN | 107205657 | A | 9/2017 |
| CN | 107223247 | A | 9/2017 |
| CN | 107257653 | A | 10/2017 |
| WO | 2019/162490 | A1 | 8/2019 |

OTHER PUBLICATIONS

International Search Report corresponding to PCT Application No. PCT/EP2019/054551, mailed May 24, 2019 (4 pages).

Bosch Sensortec, BMA280 Digital, triaxial acceleration sensor, Data Sheet, Aug. 2019, available at https://www.bosch-sensortec.com/media/boschsensortec/downloads/datasheets/bst-bma280-ds000.pdf (last accessed Aug. 21, 2020) (120 pages).

Inan, O. T. et al., "Ballistocardiography and Seismocardiography: A Review of Recent Advances," IEEE Journal of Biomedical and Health Informatics, vol. 19, No. 4, pp. 1414-1427, Jul. 2015 (14 pages).

Jiang et al., "Modeling and Simulation of Body Seismic Signals for Cardiac Dynamics," Journal of System Simulation, Mar. 2013, vol. 25, No. 3, pp. 420-424.

Huang et al., "Data Fusion Algorithm in Wearable Wireless Body Area Network," Modern Manufacturing Technology and Equipment, 2015, vol. 5, pp. 145-148.

* cited by examiner

WEARABLE HEALTH DEVICE SYSTEM WITH AUTOMATIC REFERENCING OF SEISMOCARDIOGRAPHY SIGNALS

This application is a 35 U.S.C. § 371 National Stage Application of PCT/EP2019/054551, filed on Feb. 25, 2019, which claims the benefit of priority of U.S. Provisional Application Ser. No. 62/635,824, filed on Feb. 27, 2018, the disclosures of which are incorporated herein by reference in their entirety.

FIELD

This disclosure relates generally to wearable health devices and, more particularly, to a wearable health device system with automatic referencing of seismocardiography signals.

BACKGROUND

Unless otherwise indicated herein, the materials described in this section are not prior art to the claims in this application and are not admitted as prior art by inclusion in this section.

Cardiovascular disease is among the leading causes of death. A number of diagnostic approaches have been developed to provide insight as to cardiovascular function in order to diagnose cardiovascular disease. These approaches include electrocardiography (ECG), echocardiography (ECHO), magnetic resonance imaging (MRI), and computerized tomography (CT) scan. These approaches focus on the physical structure of the heart and the electrical activities of the heart.

Another approach is auscultation which involves listening to the heart for audible sounds. Listening to the heart to detect potential issues is a developed skill which is useful in detecting certain structural issues which create unique sounds. By way of example, heart murmurs can be detected by auscultation.

An approach which differs fundamentally from the above described approaches is seismocardiography (SCG). Seismocardiography (SCG) is the detection/recording of body vibrations, typically at the sternum, which are induced by cardiovascular function. Based on these measurements, different parameters such as heart rate, heart rate variability, blood pressure estimation, cardiac output and also potential cardiovascular health problems can be identified. The information obtained through SCG may provide valuable diagnostic insight for ischemia detection, myocardial contractility, atrial fibrillation, and other cardiac issues. Because SCG is sensitive to vibrations, it can be used in diagnosing both mechanical and electrical issues related to cardiovascular function.

Unlike ballistocardiogram (BCG) techniques, which measure the forces of the body in reaction to the cardiac ejection of the blood, SCG utilizes wearable sensors such as accelerometers attached to the chest. Due to recent advancements in sensor technologies, SCG signals can be acquired with three dimensional (3D) accelerometers at a high sampling rate and bit resolution, which enables a detailed SCG evaluation. Thus, SCG evaluation is not subject to the limitation of simply summing acceleration based on cardiovascular forces (one dimension) as is the case for BCG methods.

The characteristics of the measured signals in SCG, however, are dependent on the measurement position (location and orientation of the sensor typically on the chest) and anatomical and physiological characteristics of the subject. Inter-subject variabilities are caused, e.g., by the variation in the position and orientation of the heart and the aorta between different subjects. The orientation of the various anatomical structures can vary between subjects by a number of degrees and be displaced by several centimeters. Intra-subject variability is primarily caused by translational and rotational errors after a sensor is removed and then reattached or replaced with another acceleration sensor on the chest of the same person. This results in a high inter- and intra-subject variability and makes a comparison between SCG signals difficult both between individuals and over a measurement period for a single individual. This is particularly problematic for automated evaluation routines.

In order to address the variability issues discussed above, as well as for assessment of the SCG data obtained, it is beneficial to identify cardiac cycles within the data. While this can be done manually, such identification is burdensome, particularly when a large amount of data is to be assessed.

Accordingly, it would be beneficial if output from SCG sensor devices could be automatically referenced to allow for identification of cardiac cycles within the data.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In accordance with one embodiment, a wearable health device system includes a housing configured to be worn by a subject, and a sensor assembly with at least two accelerometers which sense acceleration along non-parallel axes. A processor operably connected to the sensor assembly and a memory executes program instructions in the memory to obtain SCG template data from the accelerometers and divide the obtained SCG template data into at least one cardiac cycle segment by converting the SCG template data into polar coordinate SCG template data or spherical coordinate SCG template data. At least one reference cardiac event is identified in the SCG template data using the converted SCG template data, and the SCG template data is divided into at least one cardiac cycle segment based upon the referenced cardiac event.

In one or more embodiments, the processor is configured to execute the program instructions to identify the at least one reference cardiac event in the obtained SCG template data using the converted SCG template data by identifying a first radial amplitude in the converted SCG template data and comparing the first radial amplitude to a threshold amplitude. The processor is further configured to determine that a first cardiac event has occurred based upon the comparison of the first radial amplitude to the threshold amplitude.

In one or more embodiments, the processor is configured to execute the program instructions to convert the SCG template data into the spherical coordinate SCG template data including the first radial amplitude, a first polar angle ($\theta_1$) between the first radial amplitude and a z-axis, and a first azimuthal angle ($\varphi_1$) between the first radial amplitude and an x-axis. Identifying the at least one reference cardiac event in the obtained SCG template data using the converted SCG template data includes identifying the first cardiac event as an aortic valve opening (AO) event when $-20° \leq \varphi_1 \leq 20°$ and $70° \leq \theta_1 \leq 110°$.

In one or more embodiments, the processor is further configured to execute the program instructions to identify the at least one reference cardiac event in the obtained SCG template data using the converted SCG template data by determining that a second cardiac event has occurred based upon comparing a second radial amplitude to the threshold amplitude. Additionally, the processor is configured to execute the program instructions to convert the SCG template data into the spherical SCG template data including the second radial amplitude, a second polar angle ($\theta_2$) between the second radial amplitude and the z-axis, and a second azimuthal angle ($\varphi_2$) between the second radial amplitude and the x-axis. In these embodiments, identifying the at least one reference cardiac event in the obtained SCG template data using the converted SCG template data includes identifying the second cardiac event as a maximum force aorta (MFA) event when $-20° \leq \varphi_2 \leq 20°$ and $-20° \leq \theta_2 \leq 20°$.

In one or more embodiments, the processor is further configured to execute the program instructions to identify the at least one reference cardiac event in the obtained SCG template data using the converted SCG template data by comparing the $\varphi_1$ with the $\varphi_2$, and identifying the first cardiac event as an AO event and the second cardiac event as an MFA event when $\varphi_1+\varphi_2=90° \pm 20°$.

In one or more embodiments, the processor is further configured to execute the program instructions to identify the at least one reference cardiac event in the obtained SCG template data using the converted SCG template data by determining a difference in time between detection of the first radial amplitude and detection of the second radial amplitude, and comparing the difference in time to a time limit. The at least one reference cardiac event is identified when the difference of time is within the time limit.

In one or more embodiments, the processor is configured to execute the program instructions to convert the SCG template data into the polar coordinate SCG template data including the first radial amplitude, and a first angle based upon a polar angle between the first radial amplitude and a z-axis. Additionally, the processor is configured to execute the program instructions to convert the SCG template data into the polar coordinate SCG template data including a second radial amplitude, and a second angle based upon a polar angle between the second radial amplitude and the z-axis. In these embodiments, the at least one reference cardiac event in the obtained SCG template data is identified using the converted SCG template data when $70° \leq (\text{First angle} - \text{Second angle}) \leq 110°$.

In one or more embodiments, the processor is further configured to execute the program instructions to identify the at least one reference cardiac event in the obtained SCG template data using the converted SCG template data by determining that a second cardiac event has occurred based upon comparing the second radial amplitude to the threshold amplitude when the second radial amplitude immediately follows the first radial amplitude in the converted SCG template data.

In one or more embodiments, the system further includes at least one filter, and the obtained SCG template data is filtered by the at least one filter prior to conversion to the polar coordinate SCG template data.

In one embodiment, a method of referencing SCG data obtained by a wearable health device system begins by positioning a wearable health device on a chest of a subject and obtaining SCG template data from a first and a second accelerometer of a sensor assembly supported by a housing of the wearable health device by executing program instructions stored in a memory with a processor. The first accelerometer is configured to sense acceleration along a first axis, and the second accelerometer is configured to sense acceleration along a second axis which is not parallel to the first axis. The SCG template data is converted into one of a polar coordinate SCG template data and a spherical coordinate SCG template data and at least one reference cardiac event in the obtained SCG template data is identified using the converted SCG template data. The identified reference point is used to divide the obtained SCG template data into at least one cardiac cycle segment.

In one or more embodiments, identifying at least one reference cardiac event in the obtained SCG template data using the converted SCG template data includes identifying with the processor a first radial amplitude in the converted SCG template data which is then compared to a threshold amplitude. The processor determines that a first cardiac event has occurred based upon the comparison of the first radial amplitude to the threshold amplitude.

In one or more embodiments, converting the SCG template data into one of a polar coordinate SCG template data and a spherical coordinate SCG template data with the processor includes converting the SCG template data into the spherical coordinate SCG template data including the first radial amplitude, a first polar angle ($\theta_1$) between the first radial amplitude and a z-axis, and a first azimuthal angle ($\varphi_1$) between the first radial amplitude and an x-axis. At least one reference cardiac event in the obtained SCG template data is identified by the processor as an aortic valve opening (AO) event when $$-20° \leq \varphi_1 \leq 20° \text{ and } 70° \leq \theta_1 \leq 110°.$$

In one or more embodiments, identifying at least one reference cardiac event in the obtained SCG template data using the converted SCG template data includes determining that a second cardiac event has occurred based upon comparing a second radial amplitude to the threshold amplitude. In these embodiments, converting the SCG template data into the spherical coordinate SCG template data includes converting the SCG template data into the spherical coordinate SCG template data including the second radial amplitude, a second polar angle ($\theta_2$) between the second radial amplitude and the z-axis, and a second azimuthal angle ($\varphi_2$) between the second radial amplitude and the x-axis. At least one reference cardiac event in the obtained SCG template data is identified as a maximum force aorta (MFA) event when $-20° \leq \varphi_2 \leq 20°$ and $-20° \leq \theta_2 \leq 20°$.

In one or more embodiments, identifying at least one reference cardiac event in the obtained SCG template data using the converted SCG template data further includes comparing with the processor the $\varphi_1$ with the $\varphi_2$ and identifying the first cardiac event as an AO event and the second cardiac event as an MFA event when $\varphi_1+\varphi_2=90° \pm 20°$.

In one or more embodiments, identifying at least one reference cardiac event in the obtained SCG template data using the converted SCG template data further includes determining with the processor a difference in time between detection of the first radial amplitude and detection of the second radial amplitude, and comparing with the processor the difference in time to a time limit stored in the memory. The at least one reference cardiac event is identified when the difference of time is within the time limit.

In one or more embodiments, the method includes converting the SCG template data into the polar coordinate SCG template data including the first radial amplitude, and a first angle based upon a polar angle between the first radial amplitude and a z-axis. The method further includes converting the SCG template data into the polar coordinate SCG template data including a second radial amplitude, and a second angle based upon a polar angle between the second radial amplitude and the z-axis. The processor identifies at least one reference cardiac event in the obtained SCG template data when 70°≤(First angle−Second angle)≤110°.

In one or more embodiments, determination that a second cardiac event has occurred is based upon comparing the second radial amplitude to the threshold amplitude when the second radial amplitude immediately follows the first radial amplitude in the converted SCG template data.

In one or more embodiments, the method includes filtering the obtained SCG template data with at least one filter prior to converting with the processor the SCG template data into the polar coordinate SCG template data.

BRIEF DESCRIPTION OF THE DRAWINGS

These and other features, aspects, and advantages of this disclosure will become better understood when the following detailed description of certain exemplary embodiments is read with reference to the accompanying drawings in which like characters represent like parts throughout the drawings, wherein.

DETAILED DESCRIPTION

The following description is presented to enable any person skilled in the art to make and use the described embodiments, and is provided in the context of a particular application and its requirements. Various modifications to the described embodiments will be readily apparent to those skilled in the art, and the general principles defined herein may be applied to other embodiments and applications without departing from the spirit and scope of the described embodiments. Thus, the described embodiments are not limited to the embodiments shown, but are to be accorded the widest scope consistent with the principles and features disclosed herein.

Various operations may be described as multiple discrete actions or operations in turn, in a manner that is most helpful in understanding the claimed subject matter. However, the order of description should not be construed as to imply that these operations are necessarily order dependent. In particular, these operations need not be performed in the order of presentation. Operations described may be performed in a different order than the described embodiment. Various additional operations may be performed and/or described operations may be omitted in additional embodiments.

Figure 1:
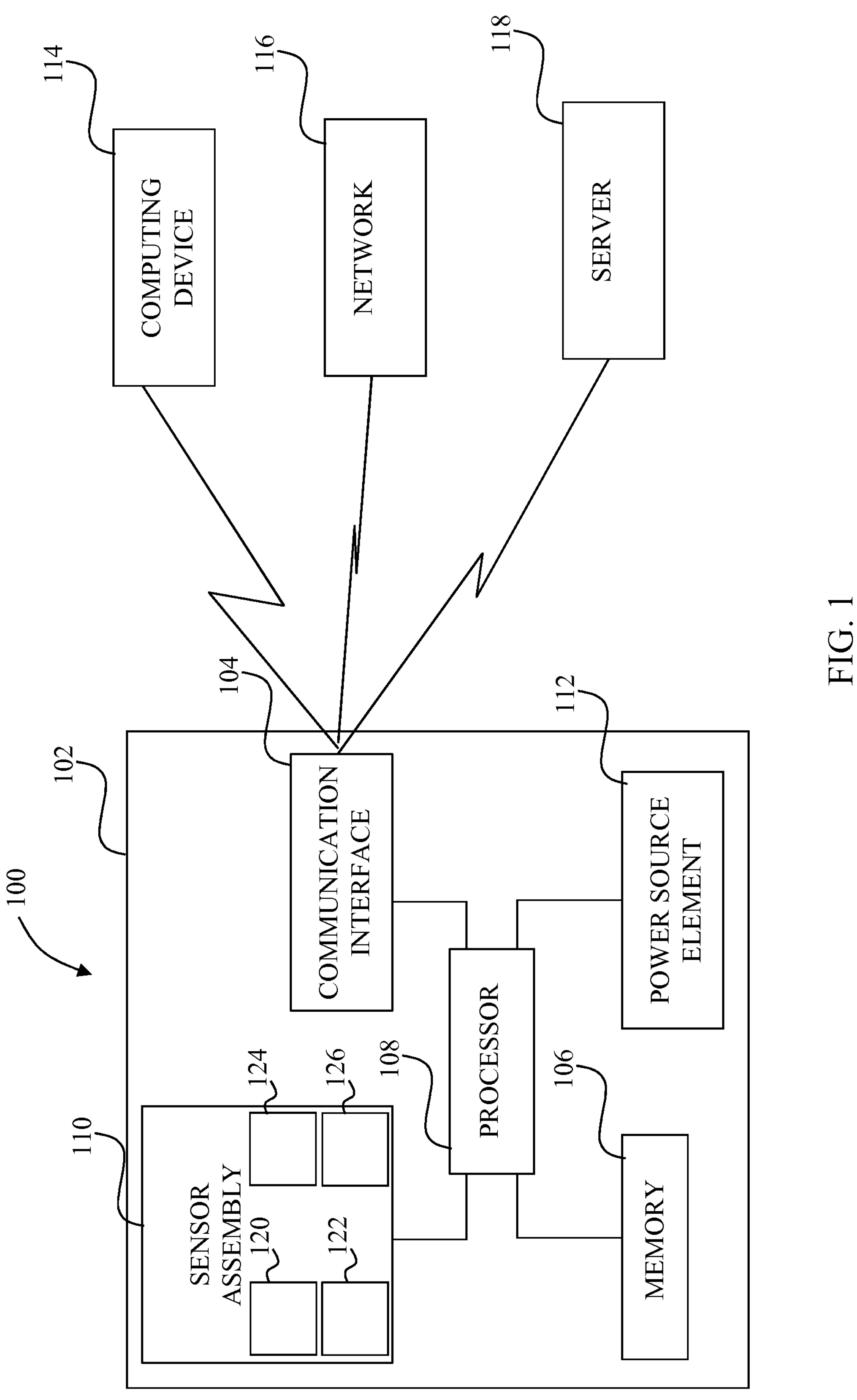
FIG. 1 depicts a block diagram illustrating a wearable health device system in accordance with a described embodiment of the disclosure.

FIG. 1 illustrates a simplified block diagram of a wearable health device 100 configured to be worn by a subject, e.g. a user, a patient, or a test subject. In use, the wearable device 100 is attached or applied to the subject's body. The wearable device 100, in one embodiment, is a patch. The wearable health device 100 includes a housing 102 which encapsulates the components of the wearable health device 100 and a suitable adhesive such as a bio-compatible double sided tape on one side or one surface of the housing 102.

As illustrated in FIG. 1, the components encapsulated in the housing of the wearable device 100 in one embodiment include a communication unit or a communication interface 104, a memory or a machine-readable medium 106, a processor or a processing unit 108, and a sensor assembly 110. In some embodiments, the wearable health device 100 includes other computer implemented modules suitable for the desired application. The computer implemented modules in one or more embodiments include an input user interface, a display, an antenna, and so forth. The wearable health device 100 is powered by a power-source element or an energy storage element 112.

The communication unit 104 forms one or more links with external computing devices 114, networks 116, and/or servers 118 so as to transfer software, data, public key, private key, and/or communication protocol between the wearable health device 100 and the devices 114, networks 116, and/or servers 118. The link is established in one or more embodiments wirelessly, by a wired communication path, and combinations thereof.

The machine 114 in different embodiments is one or more of smartphones, tablets, laptops, computers, phablets, personal digital assistants (PDAs), cellphones, voice-controlled devices such as Echo, Alexa, homepod, and the like. The network 116 in various embodiments is one or more of cloud networks, PSTNs, WANs, WLANs, and so forth.

The software, data, public key, private key, and/or communication protocol transferred to or obtained by the wearable health device 100 is stored within the memory 106. The memory 106 is a transitory machine-readable medium, non-transitory machine-readable medium, volatile machine-readable medium, non-volatile machine-readable medium, magnetic machine-readable medium, optical machine-readable medium, or electrical media, such as a random access memory (RAM), read-only memory (ROM), non-volatile RAM (NVRAM), electrically-erasable programmable ROM (EEPROM), flash memory, or any other digital or analog media.

The processor 108 in different embodiments includes one or more levels of caching, such as a level cache memory, one or more processor cores, and registers. In various embodiments the processor 108 is a microprocessor (μP), a microcontroller (μC), a digital signal processor (DSP), and any combination thereof. The exemplary processor cores may (each) include an arithmetic logic unit (ALU), a floating point unit (FPU), a digital signal processing core (DSP Core), or any combination thereof. A memory controller is used with the processor 108 in some embodiments. In some embodiments the memory controller is an internal part of the processor 108. The processor 108 is configured to execute program instructions stored in the memory 106.

Program or computer-executable instructions include, for example, instructions and data which cause a general purpose computer, special purpose computer, or special purpose processing device to perform a certain function or group of functions. Computer-executable instructions also include program modules that are executed by computers in standalone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

The energy storage element 112 in various embodiments is configured for inductive charging, qi charging, energy harvesting, wired charging, wireless charging, and any suitable charging method for transferring power to the wearable health device 100.

The sensor assembly 110 includes at least one sensor and in the embodiments depicted includes four sensors 120, 122, 124, and 126. The sensors 120, 122, 124, and 126 in different embodiments include one or more of single axis accelerometers, double-axis accelerometers, tri-axis accelerometers, gyroscopes, orientation sensors, rotation sensors, microphones, gravity sensors, ECG sensors, and so forth.

Each embodiment includes a sensor or sensors sufficient to provide acceleration sensing in at least two axes. Thus, in one embodiment, the sensors 120 and 122 are single axis accelerometers. In another embodiment, the sensor 124 is a double axis accelerometer. In one embodiment, the sensor 126 is a multi-axis accelerometer in the form of a tri-axis accelerometer. In one embodiment, the tri-axis accelerometer is model number BMA280 commercially available through Robert Bosch Sensortec of Mount Prospect, IL, USA.

Although one sensor assembly 110 is illustrated in the embodiment of FIG. 1, in other embodiments more than one sensor assembly is incorporated in the wearable health device 100 to detect and/or measure one or more parameters associated with either contractile properties of the subject's heart or the subject's blood flow.

Figure 2:
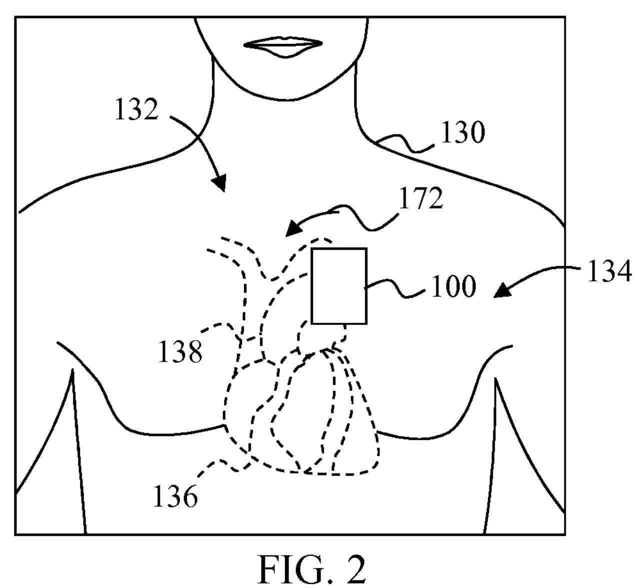
FIG. 2 depicts a plan schematic view of the wearable health device of FIG. 1 positioned on the chest of a subject.

FIG. 2 illustrates a subject 130, such as a user or a patient, which in this embodiment is a human, wearing the wearable health device 100. The wearable health device 100 in one embodiment measures the mass transit time (MTT) and/or the pulse transit time (PTT), and monitors vital signs as described in detail in U.S. application Ser. No. 15/564,585 entitled "Blood Pressure and Cardiac Monitoring System and Method", U.S. application Ser. No. 16/954,600 entitled "Vital Signs Monitoring System and Method", and PCT. Appl. Ser. No. PCT/EP2019/054549 filed the same day herewith and entitled "Wearable Health Device System With Normalized Seismocardiography Signals" which claims priority to U.S. Appl. Ser. No. 62/635,183 entitled "Compensation Method and System of Seismocardiography Signals for Wearable Health Devices", the contents of which are incorporated by reference.

As illustrated in FIG. 2, the wearable health device 100 is positioned on the chest 132 of the subject 130 at a location which is to the left of the subject's sternum (not shown for clarity sake, but located directly beneath the chin of the subject) at the upper portion of the subject's breast 134. The wearable health device 100 is positioned in one embodiment by removing or peeling off a cover from the adhesive surface of the patch before attaching the adhesive surface directly to the body of the subject 130.

At the location depicted in FIG. 2, the wearable health device 100 is typically located slightly above the heart 136 and directly over a portion of the aortic arch 138. As noted above, the actual anatomy of the individual typically varies from the depicted anatomy, and the position of the wearable health device 100 on a particular subject will also vary. When the wearable health device 100 is positioned in the manner depicted in FIG. 2, the conventional frame of reference, and the frame of reference used herein except as otherwise explicitly stated, is centered on the device 100 with the x-axis extending vertically, the y-axis extending horizontally, and the z-axis extending into/out of the page through the center of the wearable health device 100.

Figure 3:
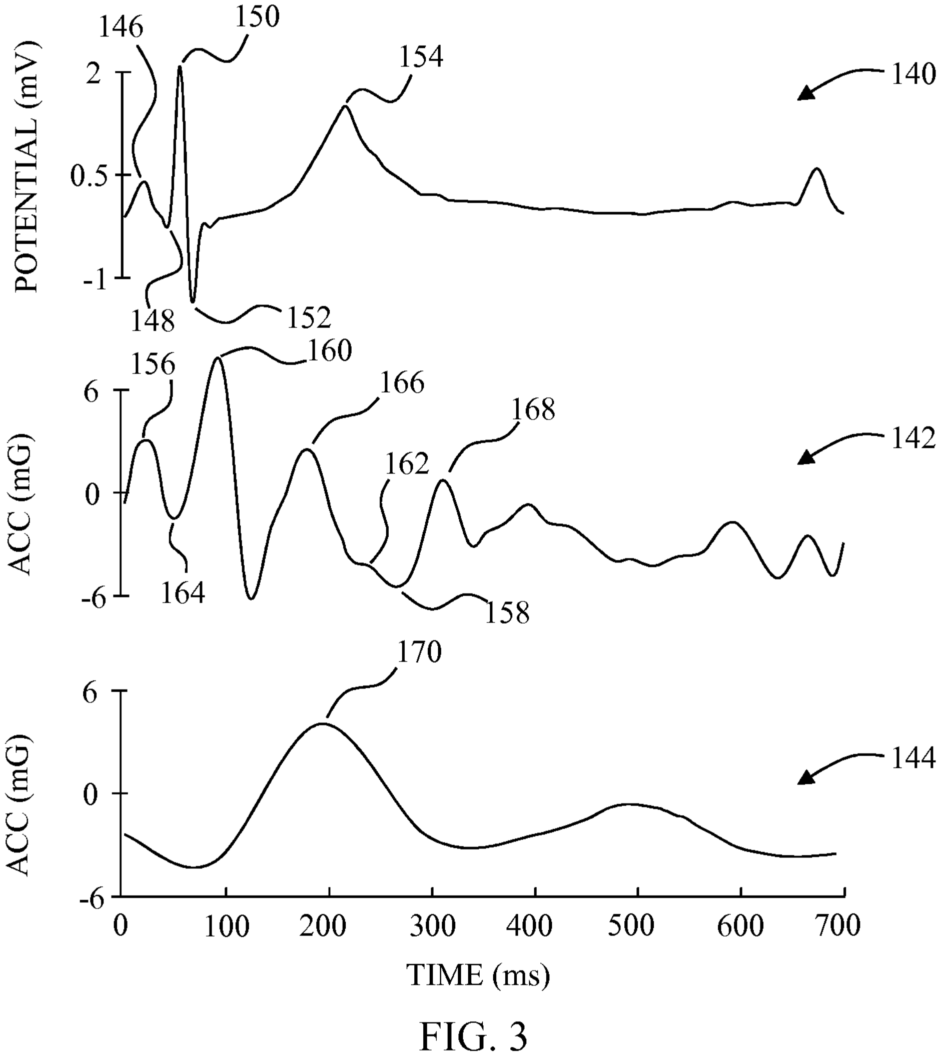
FIG. 3 depicts simplified graphs of time-dependent SCG waveforms in two axes along with a temporally synchronized ECG waveform.

The patch wearable health device 100, when activated, either manually or automatically, acquires seismocardiography (SCG) data noninvasively and continuously with a maximum of comfort and ease. FIG. 3 depicts exemplary data obtained during a single cardiac cycle from the wearable health device 100. In this embodiment, the sensor assembly includes an electrocardiogram (ECG) sensor, z-axis accelerometer, and an x-axis accelerometer. Accordingly, FIG. 3 depicts ECG data 140, z-axis data 142, and x-axis data 144. The data are temporally aligned.

Multiple local minima and maxima are discernable from FIG. 3 which provide insight as to physiological events during the cardiac cycle. The ECG data 140 shows the "P wave" 146, the "QRS complex" including the "Q wave" 148, the "R wave" 150, and the "S wave" 152. The ECG data further includes the "T wave" 154.

The z-axis data 142 reflects mitral valve closing (MC) 156, mitral valve opening (MO) 158, aortic valve opening (AO) 160, aortic valve closing (AC) 162, isovolumetric contraction (IVC) 164, rapid ejection (RE) 166, and rapid filling (RF) 168. The x-axis data 144 reflects maximum blood flow through the aortic arc which is referred to as maximum force aorta (MFA) 170.

Figures 4, 5, 6:
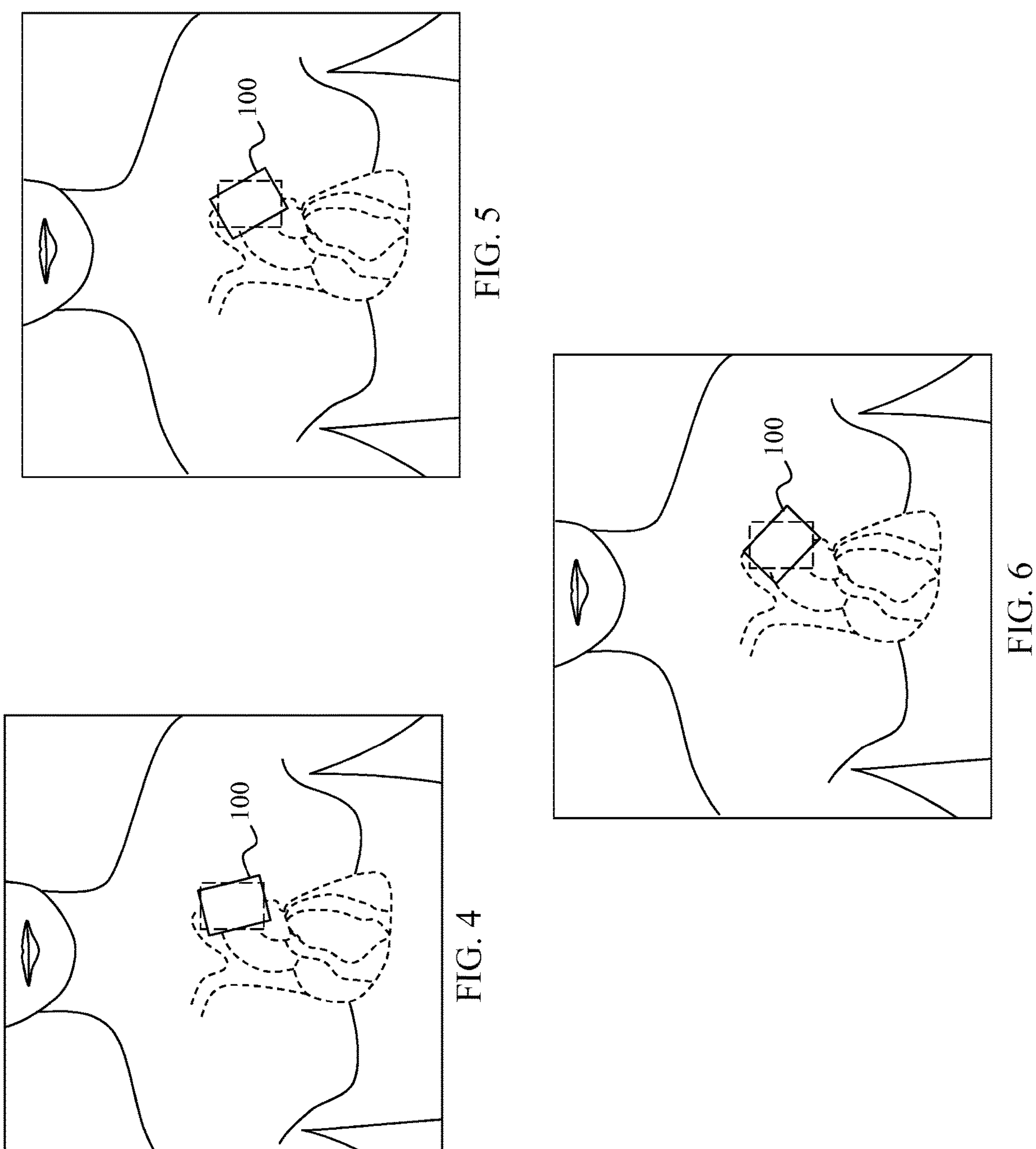
FIGS. 4-6 depict plan schematic views of the wearable health device of FIG. 1 positioned on the chest of a subject at −15°, −30°, and −45° rotations with respect to the depiction of FIG. 2.
Figure 7:
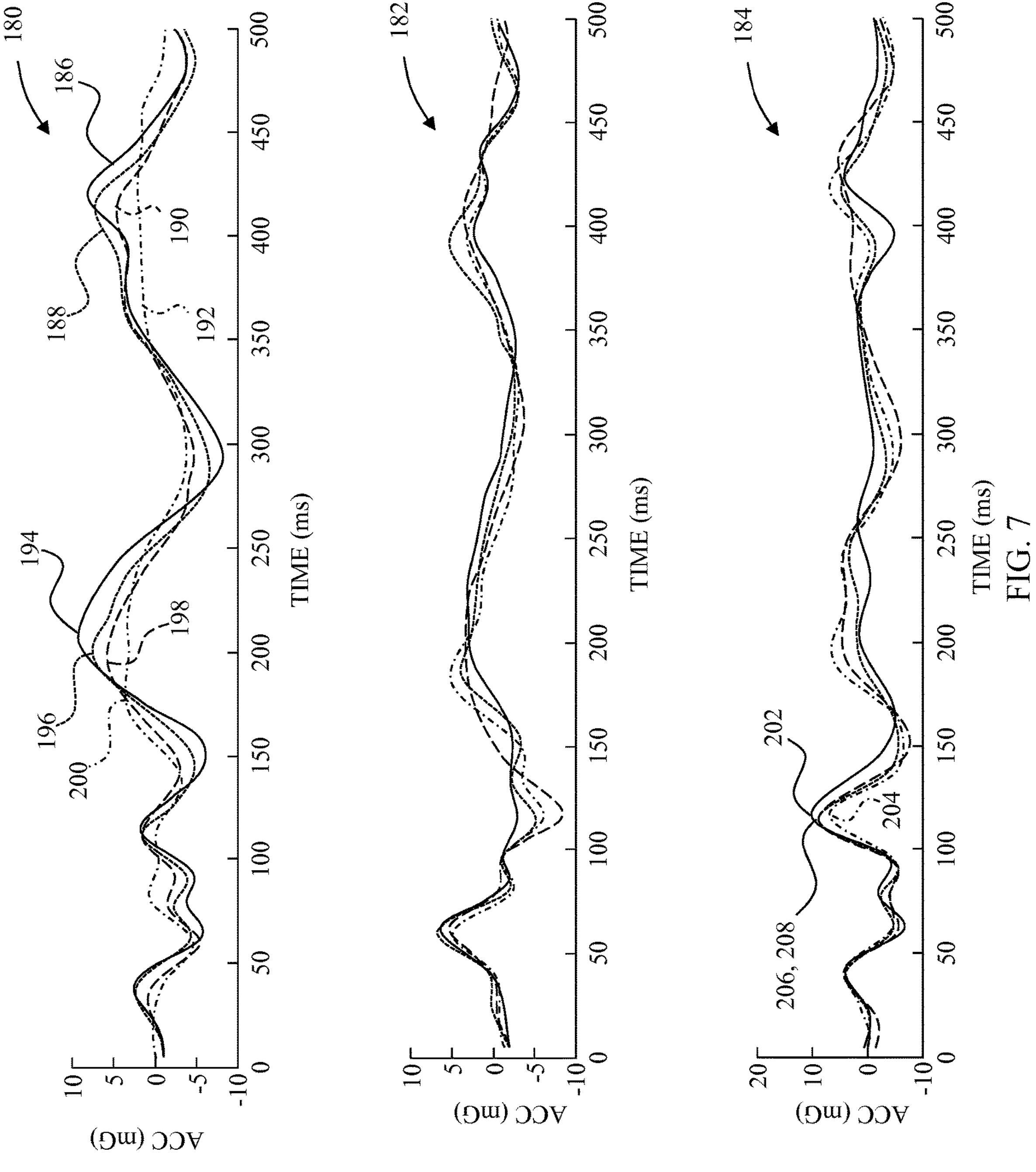
FIG. 7 depicts simplified graphs of time-dependent SCG waveforms in three different axes as detected by the wearable health device of FIG. 1 when positioned as depicted in FIG. 2, and 4-6 with the SCG signals temporally synchronized.

The prominence of the minima and maxima depends on the sensor position and orientation as well as on the anatomy of the subject. By way of example, after obtaining data with the wearable health device 100 in the position depicted in FIG. 2, the wearable health device 100 was rotated in the direction of the arrow 172 in FIG. 2 by about −15° to the position depicted in FIG. 4 and additional data was obtained. The process was repeated with the wearable health device rotated by −30° (FIG. 5) and −45° (FIG. 6). The original position of the wearable health device 100 is depicted in shadow in FIGS. 4-6. For every location, the z-axis was maintained so that the wearable health device 100 was rotated in each step by 15° about the z-axis in the negative direction. FIG. 7 depicts the data obtained from the tri-axis accelerometer 126.

FIG. 7 depicts x-axis data 180, y-axis data 182, and z-axis data 184. Each data was obtained at each of the four positions depicted in FIGS. 2 and 4-6. Thus, x-axis data 180 includes 0° rotational data 186, −15° rotational data 188, −30° rotational data 190, and −45° rotational data 192. FIG. 7 shows that as the wearable health device 100 was rotated the amplitude of the MFA peak decreased and timing of the MFA peak occurred earlier from the 0° MFA 194, to the −15° MFA 196, to the −30° MFA 198 to the −45° MFA 200.

The peak associated with the AO also showed variability as evidenced by the z-axis data 184. The amplitude of the AO peak was lowered from the 0° AO 202 to the later (temporally) −45° AO 204 while the −15° AO 206 and the −30° AO 208 amplitudes were between the 0° AO 202 and the −45° AO 204, while occurring earlier in the pattern.

The results of FIG. 7 illustrate that the orientation of the wearable health device 100 results in changes in the data observed. Likewise, movement of the wearable axis along either or both of the x-axis and the y-axis (i.e. repositioning of the z-axis) will result in amplitude and temporal changes in the observed data.

Figure 8:
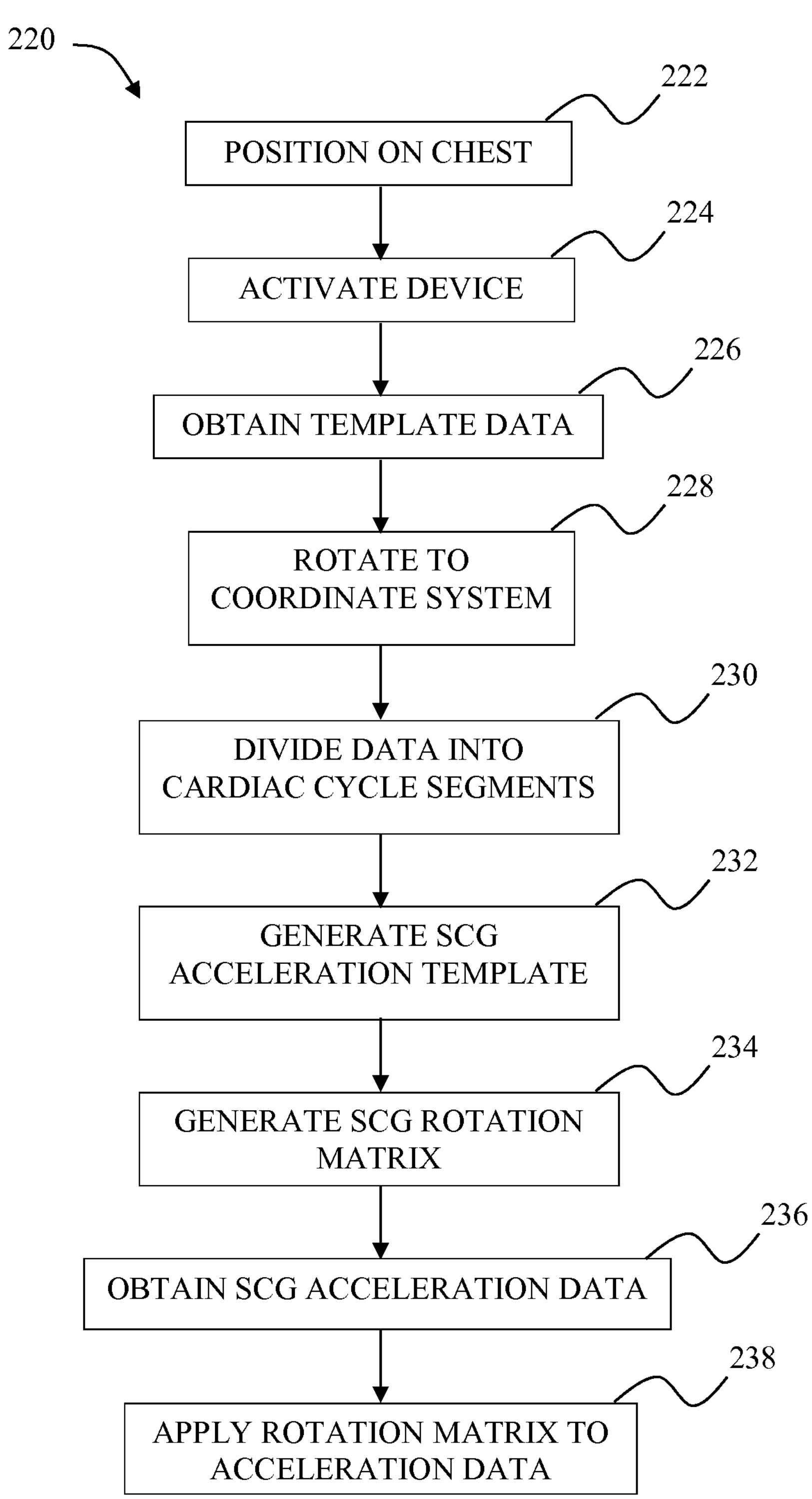
FIG. 8 depicts a process which is used in various embodiments to normalize detected SCG data from the wearable health device of FIG. 1.

Accordingly, the wearable health device 100 is configured to perform the method 220 of FIG. 8 to compensate for orientation and location differences. At block 222 the wearable health device 100 is positioned on the chest of the subject. In some embodiments attaching the wearable health device 100 (which may be a patch) onto the body of the subject includes removing or peeling a cover from an adhesive surface of the path and attaching the adhesive surface directly to the body of the subject. The wearable health device 100 is optimally positioned at the location and orientation depicted in FIG.

At block 224 the wearable health device 100 is activated either manually or automatically, and SCG template data is acquired by the sensor assembly 110 (block 226). SGC template data is SCG data acquired using one or more sensors configured to obtain data for at least two axes, preferably at least three axes. The SCG data is acquired over a period of time sufficient to obtain at least one cardiac cycle, and preferably multiple cardiac cycles and with a frequency sufficient to characterize the local maxima and minima, and stored in the memory 106. In accordance with one embodiment, the data is acquired over a period of at least 20 seconds at a frequency of at least 250 Hz.

In some embodiments, the sensor coordinate system is then rotated into a normative coordinate system at block 228 to correct for the manner in which the wearable health device 100 lays on the subject. Rotation of the coordinate system facilitates annotation of the SCG which is discussed below.

The rotation to correct for the positioning of the sensor is determined based upon gravity and the general orientation of the wearable health device 100. An example of this rotation for a three-axes device is explained with reference to FIGS. 9A and 9B. A subject will be sitting, standing, or laying down when initial data is acquired. In both a sitting and standing position, the wearable health device 100 will have the general orientation shown with respect to the subject 130' in FIG. 9A. In this position, the x-axis 240 of the wearable health device 100 is close to the gravity axis 242. The angle of rotation 244 for the x-axis is thus determined using either a gravity sensor in the sensor assembly 110 or an external instrument so as to align the rotated x-axis of the wearable health device 100 with gravity 242. The z-axis 246 of the wearable health device 100 is also modified to a rotated z-axis 248 by an identical angle of rotation 250.

A similar rotation occurs when the subject is laying down. In this scenario depicted with the subject 130" of FIG. 9B, however, the z-axis 246 of the wearable health device 100 is closest to the gravity axis 242. The angle of rotation 252 for rotation of the z-axis 246 is thus determined using either a gravity sensor in the sensor assembly 110 or an external instrument to align the rotated z-axis with gravity 242. The x-axis 240 of the wearable health device 100 is also modified to a rotated x-axis 248 by an identical angle of rotation 254.

Figures 9A, 9B:
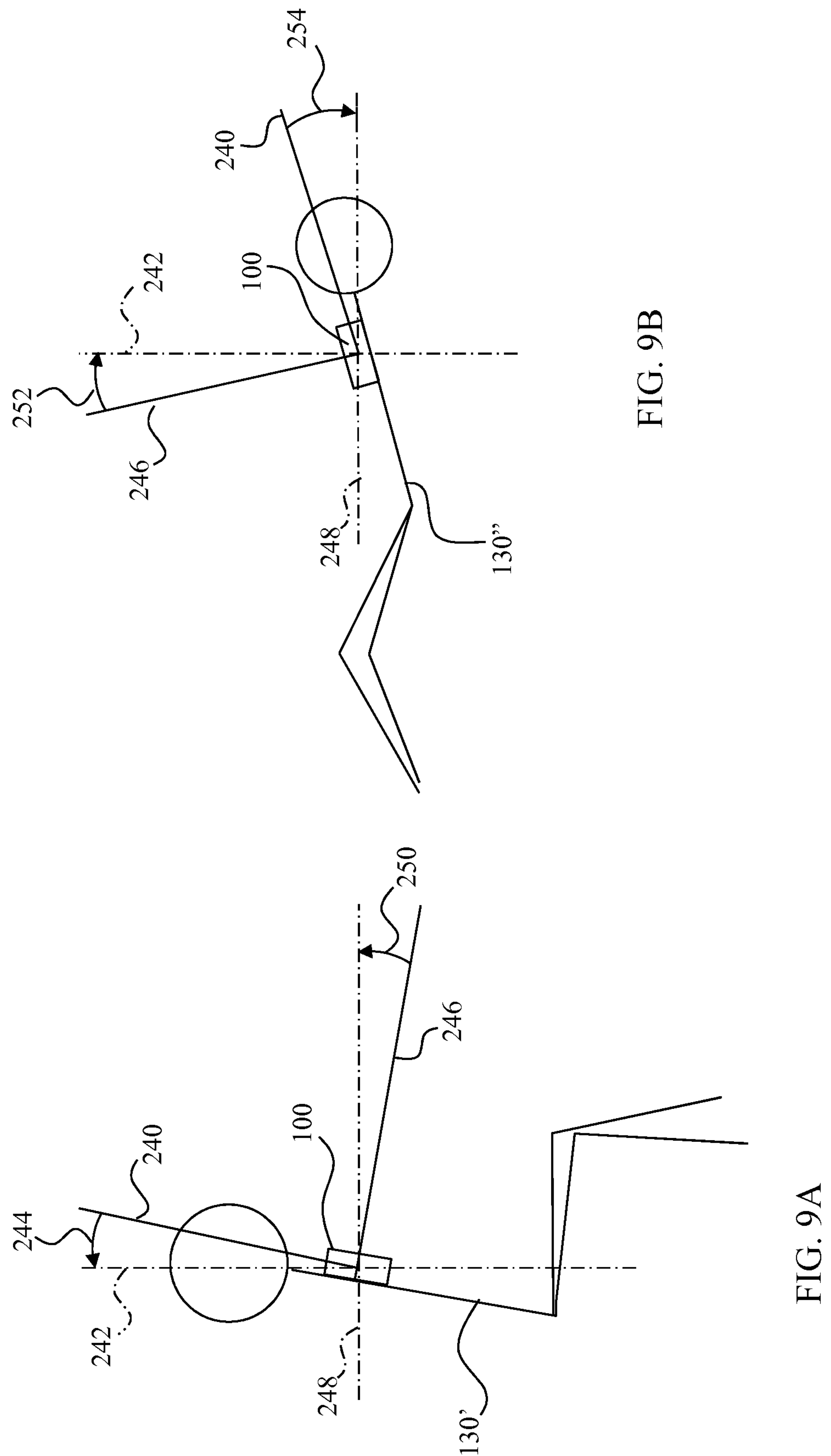
FIGS. 9A and 9B depict different poses of an individual with the wearable health device of FIG. 1 attached to illustrate a sensor axes rotation correction that is optionally included in the process of FIG. 8.

In both scenarios depicted in FIGS. 9A and 9B, the y-axis of the wearable health device 100 is assumed to be perpendicular to the gravity axis 242. Preferably, this is ensured by proper positioning of the subject prior to obtaining the data in block 224. With the known angles of rotation, along with the knowledge of which axis was rotated to align with the gravity axis 242, the obtained data can be converted to any desired world coordinate system. In embodiments incorporating attitude sensors in the sensor assembly 110, the y-axis in some embodiments is corrected based upon the gravity axis. In some embodiments, the sensor axes rotation data is stored in the memory 106. In other embodiments, the sensor axes rotation data is stored in a remote memory such as a memory associated with the computing device 114, the network 116, or the server 118, and applied to data received from the wearable sensor device 100.

Returning to FIG. 8, the obtained data is divided into cardiac cycle segments with each cardiac cycle segment including a single cardiac cycle (block 230). The segmentation is based upon any desired reference cardiac event, referred to herein as a "reference point". As discussed in more detail below, the reference point is automatically identified by the wearable health device 100 using one or more characteristic SCG points.

At block 232 an SCG acceleration template is generated using the cardiac cycle segments. Initially, the cardiac cycle segments are interpolated to a unit length and the arithmetic average is aggregated to provide an average cardiac cycle segment. The average cardiac cycle segment includes all of the data for the two or more, preferably three, axes of the accelerometers of the wearable health device 100.

The average cardiac cycle segment is then rotated to identify the orientation in three dimensional space at which the selected reference point is at a maximum in the associated axis, typically the x-axis or z-axis. In some embodiments, two or more rotations are used for the same SCG data for various purposes. Rotation of the average cardiac cycle segment to generate a rotation matrix is accomplished by transforming the sensor data from a Cartesian coordinate system into a polar coordinate system (transformation of the data from x/y/z axes into amplitude/angle representation) as discussed in more detail below. Based on these angle values a rotation matrix is computed in one embodiment by the processor 108 using an Euler angles convention.

An SCG rotation matrix based upon the rotation matrix is generated (block 234) and stored. The SCG rotation matrix, which in some embodiments incorporates the sensor axes rotation data, is stored in the memory 106. In some embodiments, more than one rotation matrix is generated for a given set of data so as to optimize the normalized data to different reference points. In some embodiments, the rotation matrix is stored in a remote memory such as a memory associated with the computing device 114, the network 116, or the server 118, and applied to data received from the wearable sensor device 100.

The wearable health device 100 is then used to collect SCG acceleration data at block 236. SCG acceleration data is SCG data acquired using at least the one or more sensors used to obtain SCG template data. In some embodiments, collection of the SCG acceleration data is accomplished prior to block 228, or at any other desired time including before block 226. The SCG acceleration data is stored in the memory 106 or transmitted in real time or near real time to one or more of the computing device 114, the network 116, or the server 118. The SCG acceleration data typically includes a substantially larger amount of data than the SCG template data and can include the SCG template data.

At block 238 the SCG rotation matrix, and optionally the sensor axes rotation, is applied to the collected SCG acceleration data to generate normalized SCG acceleration data. In some embodiments the SCG rotation matrix, and optionally the sensor axes rotation, is applied prior to storing the data. The normalized SCG acceleration data in some embodiments is provided in a database with other normalized SCG acceleration data. Because the data has been normalized, more accurate comparisons can be made since sensor placement errors (orientation of the accelerometers) and anatomical variations between subjects (orientation of the aortic arch) are accounted for. The normalization method is generic and can be used in different applications.

Moreover, the normalized SCG data is used in some embodiments to estimate the position and orientation of certain anatomical structures such as the aortic arc. Specifically, a rotation vector is computed based on the generated SCG acceleration template. The rotation vector points toward the location of the anatomical reference point. Accordingly, by generating the SCG acceleration template using the MFA as the selected reference point, the rotation vector for the peak points toward the aortic arc. If the position and orientation of the sensor on the chest is known, the orientation of the anatomic reference structure can be estimated. The accuracy of this procedure can be further improved by the acquisition of SCG data at different chest positions.

Thus, the disclosed method can be further used to estimate the orientation of anatomical structures (e.g. aortic arc). In contrast to expensive imaging techniques (e.g. MRT), the disclosed method is inexpensive and can be performed outside hospital environments.

Figure 10:
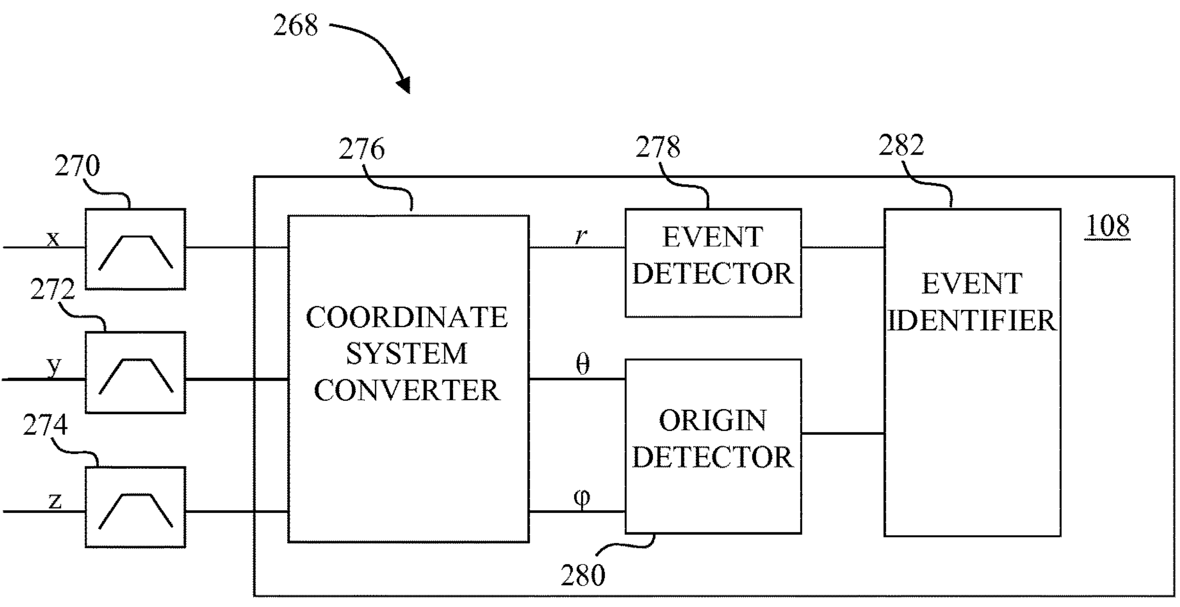
FIG. 10 depicts a schematic diagram of the reference point identifier circuit which in one embodiment is provided in the processor of FIG. 1.

As noted above, the reference point or points used in dividing the template data into cardiac cycle segments is identified automatically by the wearable health device 100 as discussed in reference to FIG. 10. FIG. 10 depicts a reference point identifier circuit 268 wherein the x-, y-, and z-axis SCG data from the sensor assembly 112 is passed through filters 270, 272, and 274, respectively. The filters 270, 272, and 274, which in some embodiments are incorporated within the sensor assembly 112, are configured in any desired manner. Typically a high-pass or bandpass filter is incorporated to reduce bandwidth and reduce gravity vector interference. The input signals in some embodiments are additionally/alternatively low-pass or bandpass filters which are used to reduce noise and reduce gravity vector interference thereby improving accuracy.

The preferably filtered signals and timing data are then passed to the processor 108 which includes coordinate system converter module 276, event detector module 278, origin detector module 280, and event identifier module 282. In some embodiments the coordinate system converter module 276, event detector module 278, origin detector module 280, and event identifier module 282 are provided separately from the processor 108. Operation of the reference point identifier circuit 268 is further explained with reference to the procedure 300 of FIG. 11.

Figure 11:
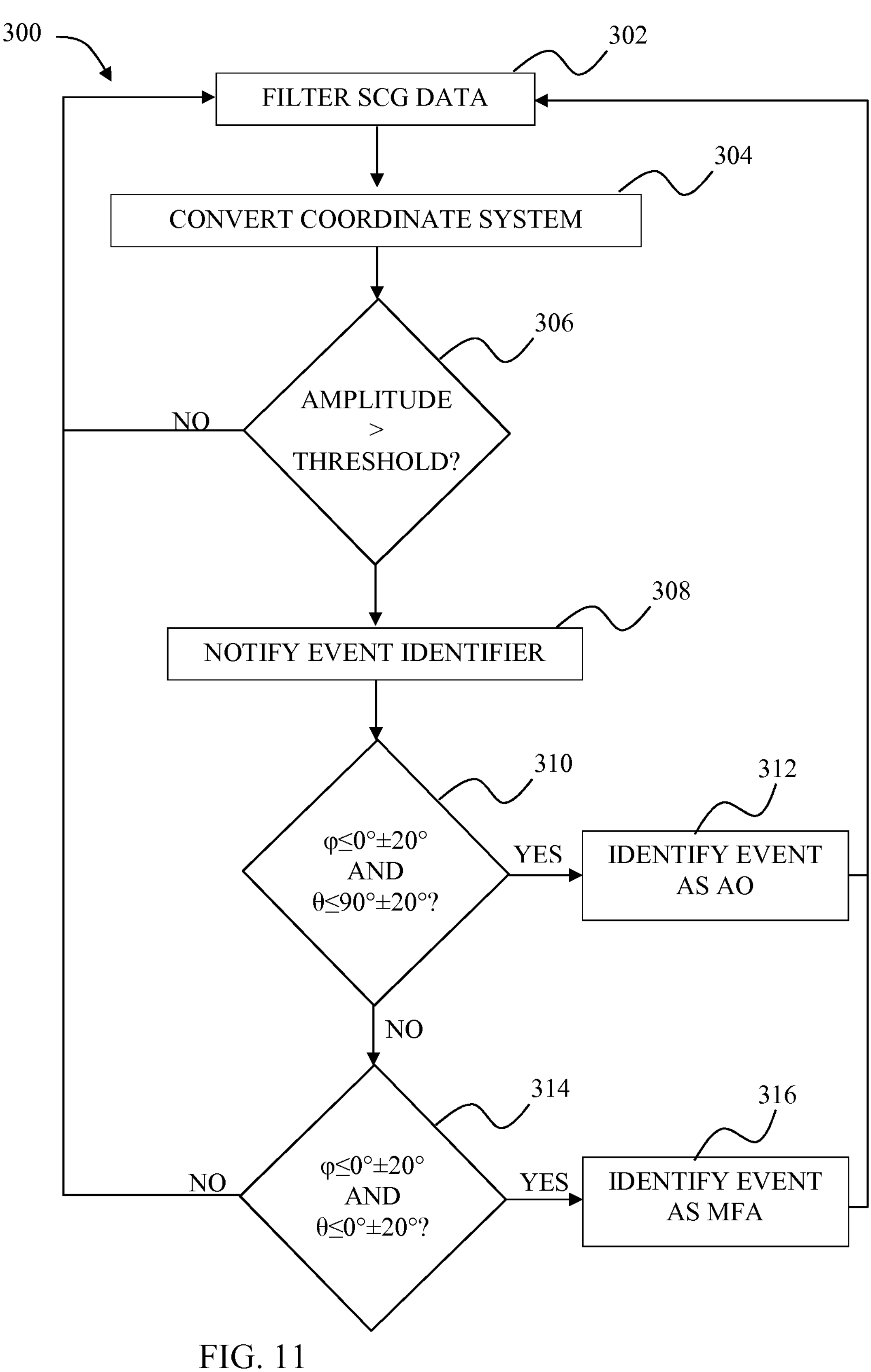
FIG. 11 depicts a process executed by the processor of FIG. 1 using the reference point circuit of FIG. 10 to automatically identify reference points in SCG data which has been converted to a spherical coordinate system.

In FIG. 11, the procedure 300 begins with filtering of the SCG data from the sensor or sensors 120, 122, 124, 126 used to obtain the acceleration data using two or more filters such as the filters 270, 272, and 274 (block 302). The filtered SCG data is then passed to the coordinate system converter module 276 which converts the SCG data to either a polar or spherical coordinate system (block 304). More particularly, the coordinate system converter module 276 converts the Cartesian coordinates (x, y, z) to polar (two dimensional when only two axes are provided) or spherical (three dimensional when three axes are used) coordinates. In one embodiment, conversion from Cartesian to spherical coordinates is accomplished in accordance with the International Organization for Standardization (ISO) physics convention by execution of program instructions in the memory 106 by the processor 108 which is described with reference to FIG. 12.

Figures 12, 13:
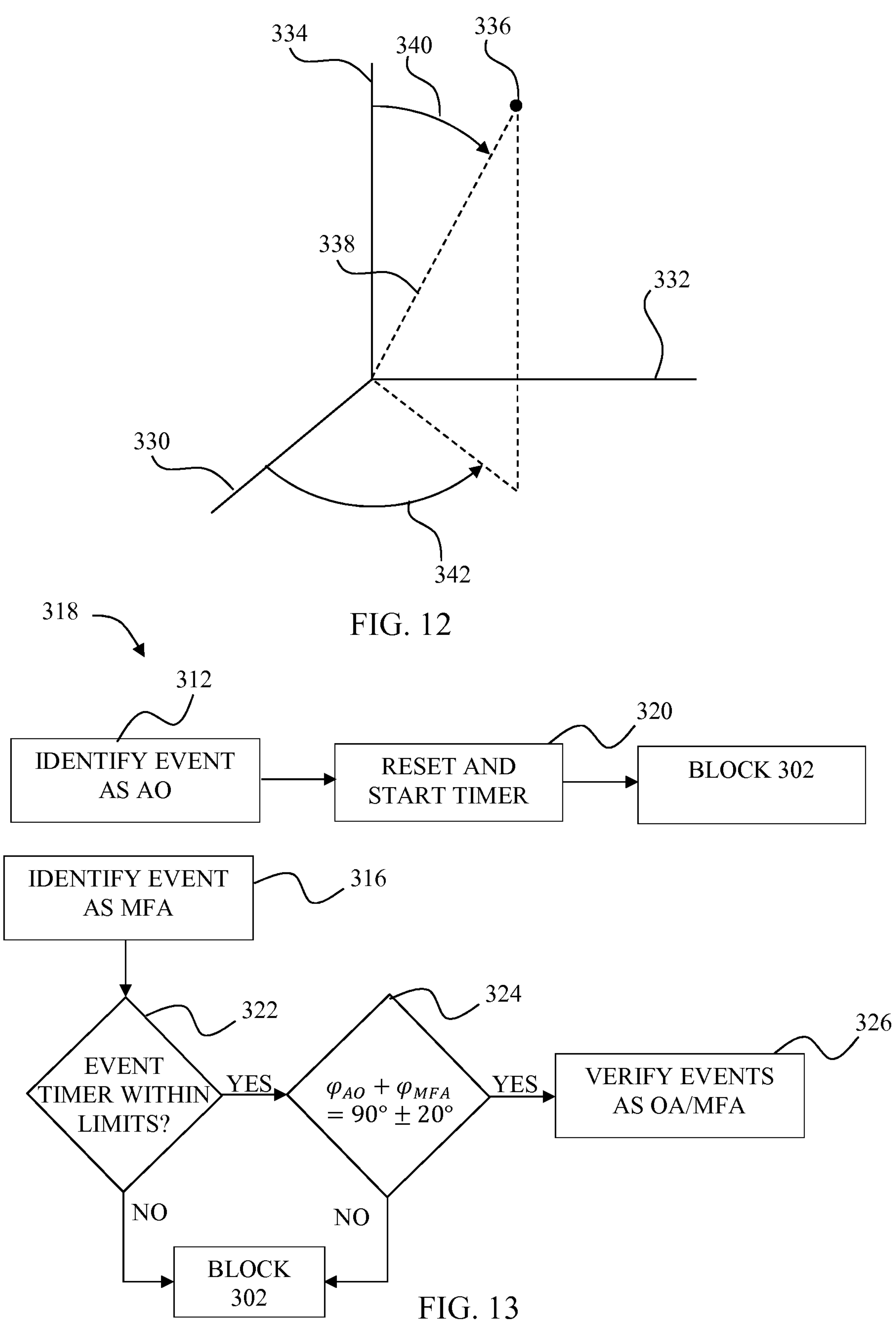
FIG. 12 depicts a graph of a spherical coordinate system into which SCG data is converted by the process or FIG. 1 during the process of FIG. 11.
FIG. 13 depicts sub processes or routines executed by the processor in some embodiments during the execution of the process of FIG. 11.

FIG. 12 depicts an x-axis 330, a y-axis 332 and a z-axis 334 which in one embodiment corresponds to the three axes sensed by the wearable health device 100. Accordingly, the x-y plane represents the chest of the subject 130. The (x, y, z) SCG data from the 3D accelerometer in the sensor assembly identify a point 336. The point is also defined in a spherical coordinate system by a radius (r) 338 and two angles θ (340) and φ (342). The angle θ (340) is the polar angle identifying the angle between the z-axis and the amplitude or radius 338. The angle φ (342) is the azimuthal angle identifying the angle between x- and y-axes coordinates of the amplitude or radius 338 and the x-axis. The radius (r) 338 is computed using the Cartesian coordinates (x, y, z) based on the following equation:

$$r = \sqrt{x^2 + y^2 + z^2}$$

Calculation of the angles 340 and 342 is thus in accordance with the following equations:

$$\theta = \arccos\left(\frac{z}{r}\right)$$

$$\varphi = \arccos\left(\frac{y}{x}\right)$$

Accordingly, the processor 108/coordinate system converter module 276 converts the Cartesian coordinates (x, y, z) to the spherical coordinates (r, θ, φ).

Returning to FIG. 11, the radius (r) 338 is passed to the event detector 278 which compares the amplitude of the radius (r) 338 to a predetermined threshold (block 306). If the amplitude of the radius (r) 338 does not meet the threshold, the process returns to block 302 and the next SCG data is received. If the amplitude of the radius (r) 338 exceeds (or meets in some embodiments) the threshold, then the event identifier 282 is notified of the occurrence and time of an event (block 308) and evaluates input from the origin detector 280 to identify the event.

In particular, the origin detector 280 receives the angles θ (340) and φ (342) from the coordinate system converter module 276. The origin detector module 282 compares the received angles θ (340) and φ (342) to values stored in the memory 106 to determine if the received angles θ (340) and φ (342) may be associated with an SCG reference point by comparing the SCG data with known relationships. For example, with an AO event, φ≤0° and θ≤90° after gravity reduction through the filters 270, 272, and 274. For an MFA event, φ≤0° and θ≤0° after gravity reduction through the filters 270, 272, and 274. Moreover, AO and MFA are separated by about 90° in the angle φ (342).

As discussed above, the SCG data is affected by the position and orientation of the wearable health device on the subject. Accordingly, the origin detector module 282 will typically incorporate an error range in assessing the angles θ (340) and φ (342). In one embodiment, the error range is selected to be up to 20° to account for positioning errors while minimizing potential identification errors. Accordingly, the origin detector module 282 indicates an AO event if φ≤0°±20° and θ≤90°±20° after gravity reduction through the filters 270, 272, and 274 (block 310). The event identifier module 282 then identifies the event as an AO event (block 312) and the process returns to block 302.

If at block 310 the angle requirements for an AO event are not met, then the process 200 continues to block 314 and the origin detector module 282 indicates an MFA event if φ≤0°±20° and θ≤0°±20° after gravity reduction through the filters 270, 272, and 274. The event identifier module 282 then identifies the event as an MFA event (block 316) and the process returns to block 302. If at block 314 the angle requirements for an MFA event are not met, then the process 200 continues to block 302.

The procedure 300 is modified based upon the particular reference point or points to be used. Moreover, the SCG data can be further evaluated to provide higher certainty that the detected event is the identified event. By way of example, as noted above AO and MFA are about 90° separated in the angle φ. Moreover, as depicted in FIG. 7, the OA peaks 202, 204, 206, and 208 precede the MFA peaks 194, 196, 198, and 200. Accordingly, in some embodiments the procedure 300 further includes part or all of the sub-process 318 of FIG. 13.

In sub-process 318, each time an AO event is identified at block 312, an event timer is reset and started at block 320 prior to the process returning to block 302. Additionally, each time an MFA event is identified at block 316, the event timer is checked at block 322, although in some embodiments checking the timer is omitted. If the event timer is not within the limit associated with the timing of the AO and MFA peaks, the process returns to block 302. If the event timer is within the limit associated with the timing of the AO and MFA peaks (typically about 100 ms plus/minus an error range which in some embodiments is 20 ms), the process continues to block 324.

At block 324, the value of the angle φ for the AO event and the value of the angle φ for the MFA are summed to verify that the sum is about 90°. Block 324 shows incorporation of the range of +/−20° which was used in the procedure 300 is also incorporated in the sub-process 318. If the AO and MFA are not about 90° separated in the angle φ, the process returns to block 302. If the AO and MFA are about 90° separated in the angle φ, the events are verified as AO and MFA events (block 326). Accordingly, either, or both, of the events is then used as a reference point in analyzing the SCG data.

Moreover, since the MFA and AO peaks have been identified in the filtered SCG data, then any of the other features in the unfiltered SCG data can be automatically identified simply by analyzing the timing, maxima, and minima of the signal with respect to the maxima or minima associated with the identified reference point or points. Thus, the wearable health device 100 can automatically segment the SCG data into cardiac cycle segments. For example, once the AO peak 160 in the data of FIG. 3 is identified as a reference point, the remaining maxima and minima of FIG. 3 can be ascertained based upon known relative relationships to the AO peak 160. Alternatively, the data can be segmented using subsequent AO peaks identified as reference points in the manner described above.

While the procedure 300 was explained with reference to a spherical system, the procedure 300 is practiced in a polar system in some embodiments. Additionally, the coordinate system in some embodiments is reduced to a planar system for analysis by setting the system to the z-x plane for the event identification (e.g., AO identification) with the angle θ used as the event identifier and the angle φ set at zero. Accordingly, only the timing and difference in the angle θ (90°+/−20°) is used to identify the AO/MFA pair. Moreover, because only the difference between the angles θ is used, the angle complementary to the angle θ is used in some embodiments.

Figure 14:
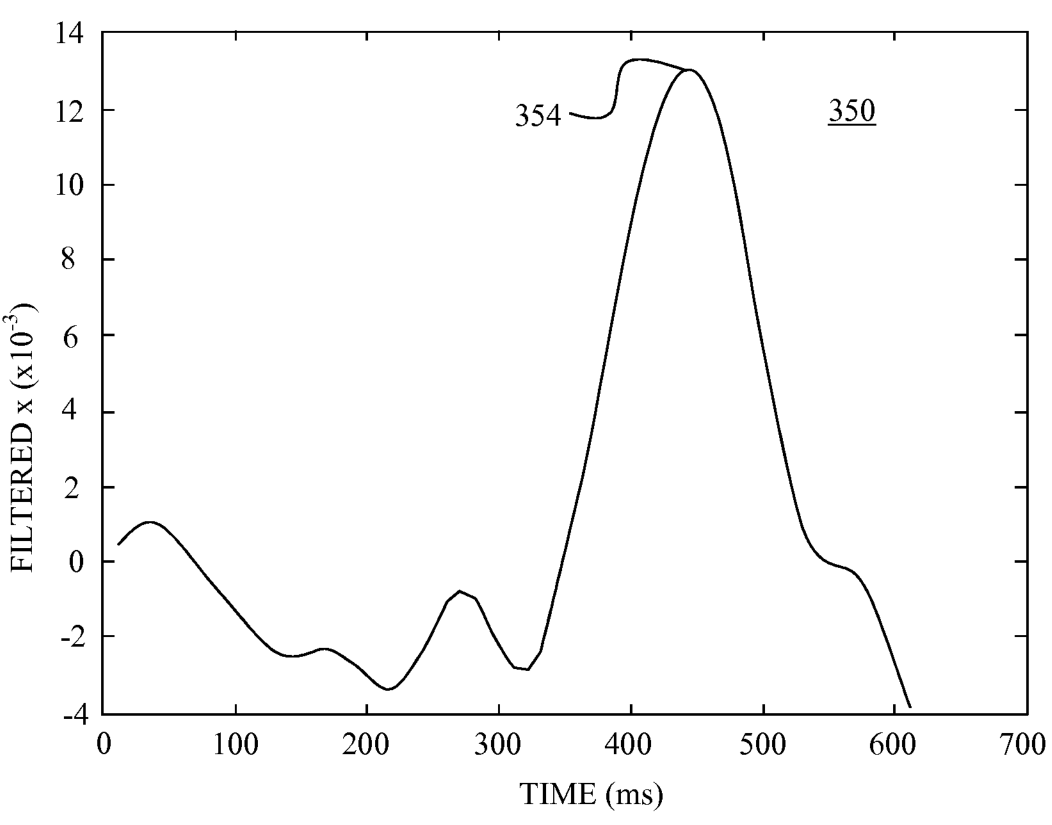
FIG. 14 depicts a graph of filtered x-axis accelerometer data and filtered z-axis accelerometer data which is provided to the circuit of FIG. 10.
Figure 14:
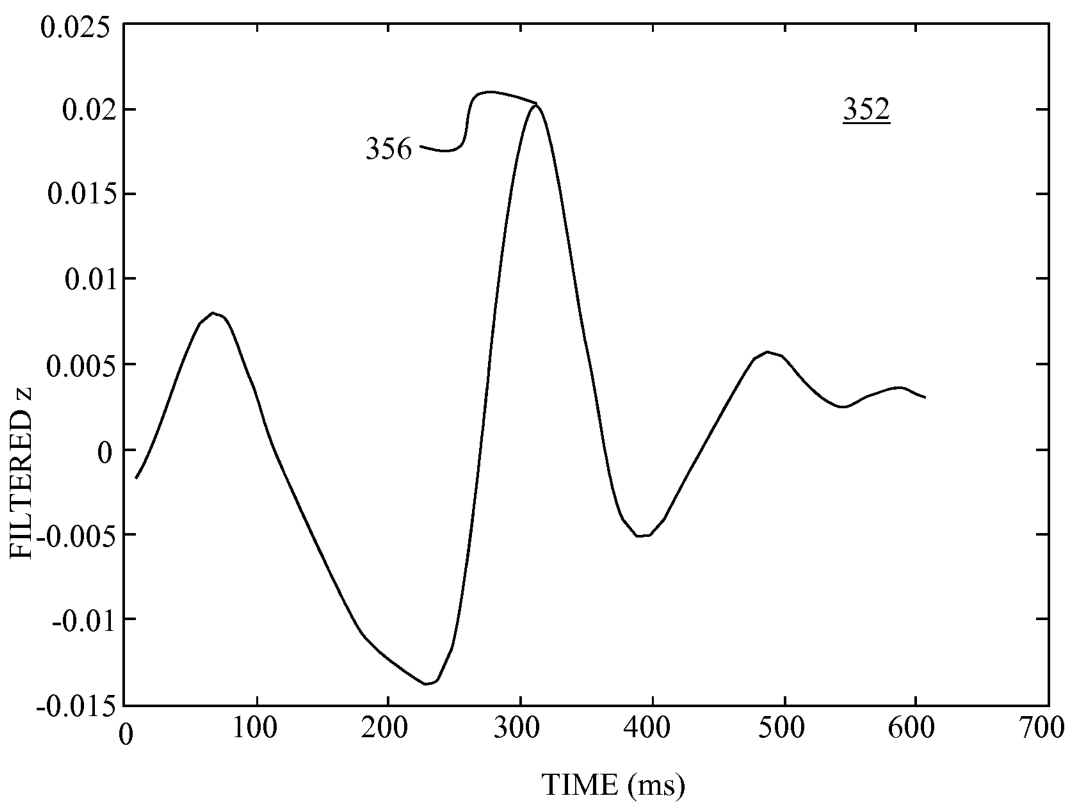
Figures 15, 16, 17:
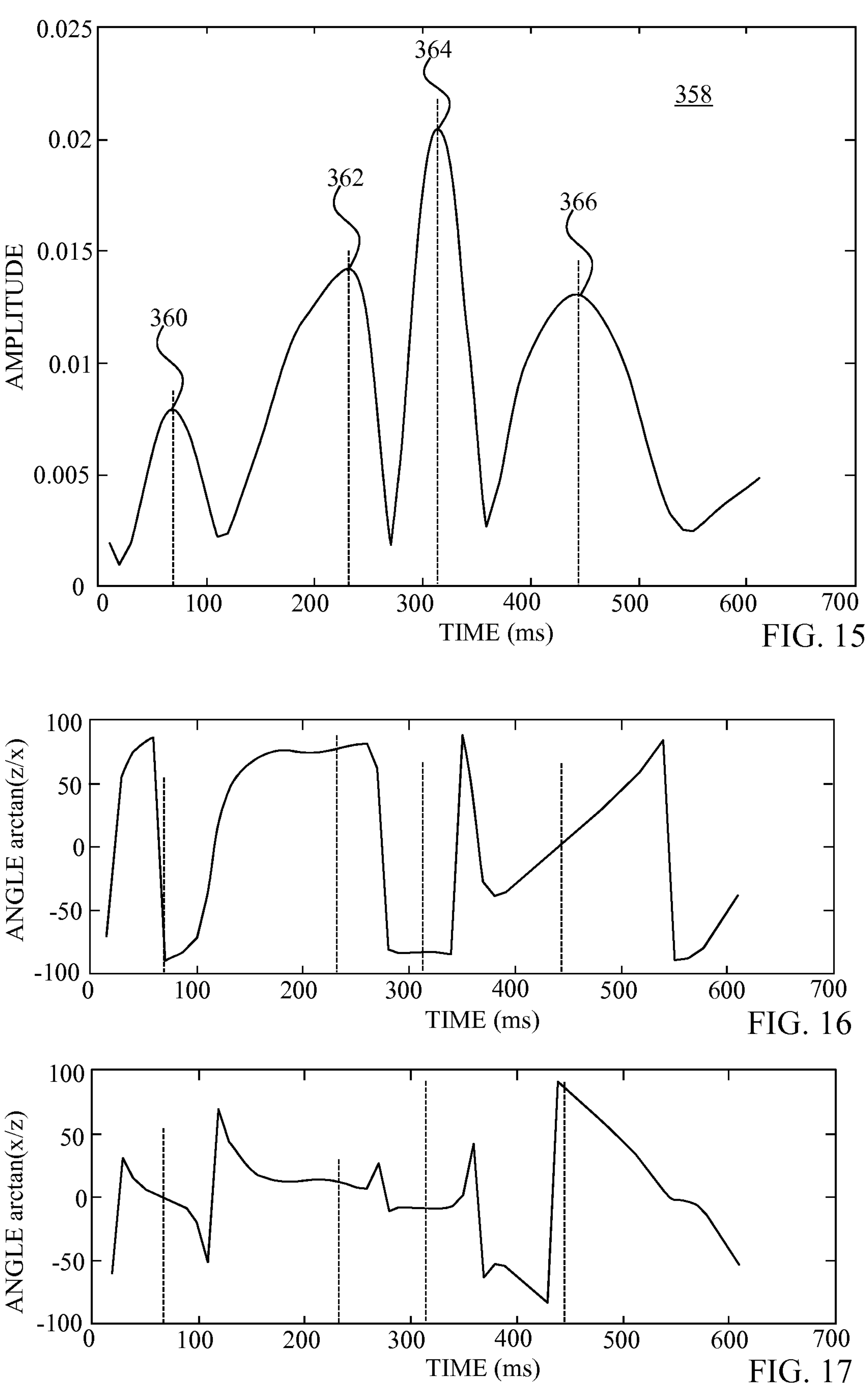
FIG. 15 depicts peaks which are generated based upon the filtered data of FIG. 14 when converting the data to a polar coordinate system.
FIG. 16 depicts the calculated angle complementary to the polar angle of the converted data from FIG. 14.
FIG. 17 depicts the calculated polar angle of the converted data from FIG. 14.

By way of example, FIG. 14 depicts filtered x-axis SCG data 350 and filtered z-axis SCG data 352. In FIG. 14, the peak 354 is an MFA peak while the peak 356 is an AO peak. The amplitude of the resultant vector for the filtered SCG data of FIG. 14 was calculated in the same manner discussed above for the spherical coordinates using only the x- and z-axes data resulting in the amplitude data 358 of FIG. 15. The filtered SCG data results in four peaks 360, 362, 364, and 366. FIG. 16 depicts the calculated angle which is complementary to θ (arctan (z/x)) for the filtered SCG data of FIG. 14 while FIG. 17 depicts the angle θ (arctan (x/z)).

Figure 18:
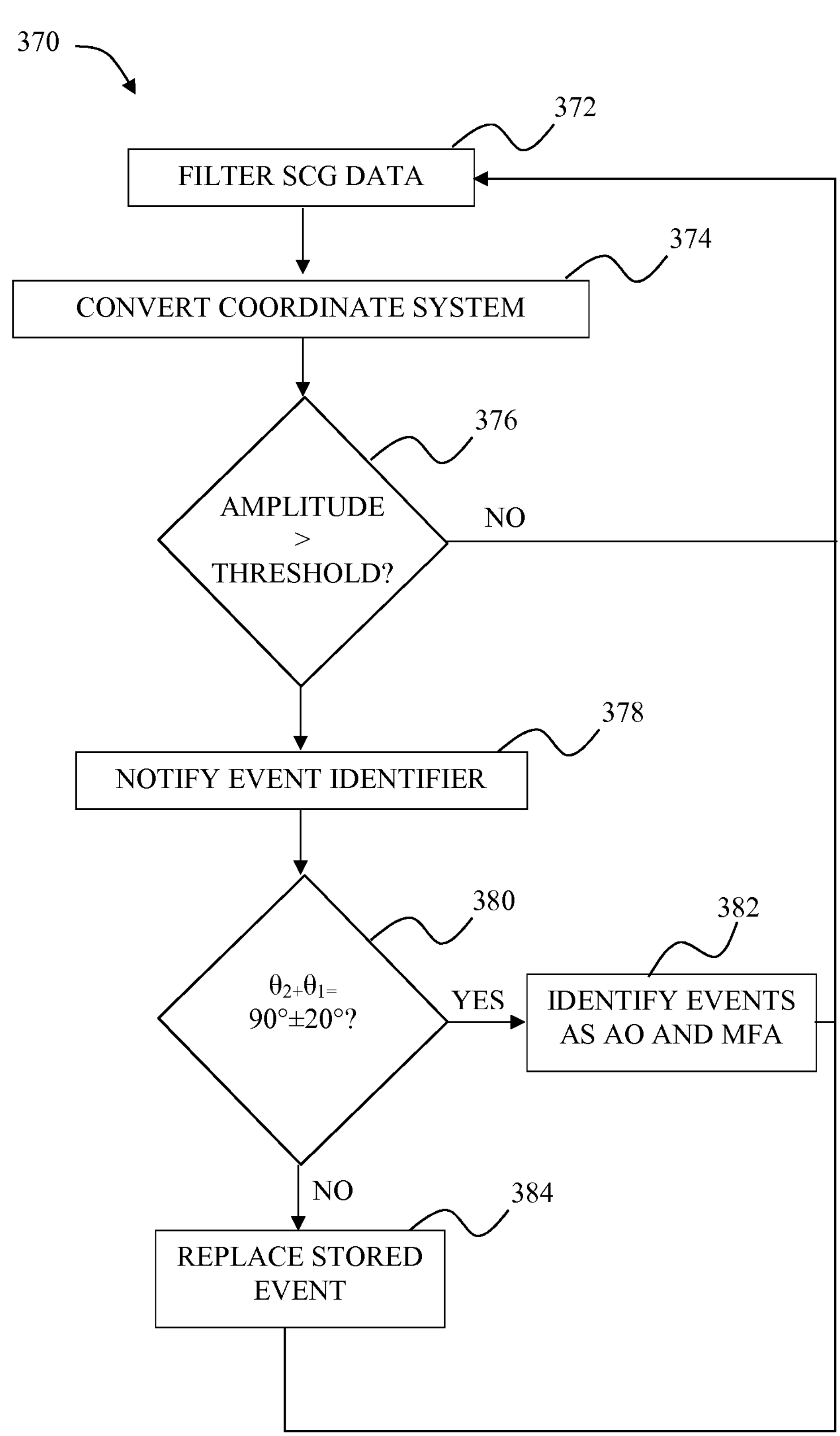
FIG. 18 depicts a process executed by the processor of FIG. 1 using the reference point circuit of FIG. 10 to automatically identify reference points in SCG data which has been converted to a polar coordinate system.

The data of FIGS. 15-17 is analyzed by the processor 106 in one embodiment in accordance with the procedure 370 of FIG. 18. At block 372 the SCG data from the sensor or sensors 120, 122, 124, 126 used to obtain the acceleration data is filtered using two or more filters such as the filters 270, 272, and 274. The filtered SCG data and timing data is then passed to the processor 108/coordinate system converter module 276 which converts the SCG data to a polar coordinate system (block 374). This is similar to the manner in which the process of FIG. 11 converts data. Since only two axes are analyzed, however, the radius (r) 338 is computed using the Cartesian coordinates (x, z) based on the following equation:

$$r = \sqrt{x^2 + z^2}$$

Calculation of the angle 342 is not necessary since it is set to "0" as there is no y-axes data used. The angle 340, and/or its complementary angle, is calculated in accordance with the following equations:

$$\theta = \arctan\left(\frac{z}{x}\right)$$

$$\text{Angle complementary to } \theta = \arctan\left(\frac{x}{z}\right)$$

Accordingly, the processor 108/coordinate system converter module 276 converts the Cartesian coordinates (x, z) to the polar coordinates (r, θ) or the complementary angle.

Returning to FIG. 18, the radius (r) 338 is passed to the event detector 278 which compares the amplitude of the radius (r) 338 to a predetermined threshold (block 376). If the amplitude of the radius (r) 338 does not meet the threshold, the process returns to block 372 and the next SCG data is received. If the amplitude of the radius (r) 338 exceeds (or meets in some embodiments) the threshold, then the event identifier 282 is notified of the occurrence of an event and obtains the calculated angle 340 or its complementary angle from the origin detector 280 (block 378).

At block 380 the event identifier 282 adds the angle associated with the notified event ($\theta_2$) to an angle from a previously stored event ($\theta_1$) and determines if the sum is 90°±20°. If the summation of the angles is 90°±20°, then at block 382 the notified event is identified as an MFA event and the previously stored event is identified as an AO event. The process 370 then continues at block 372.

If at block 380 the sum of the angles is not 90°±20°, then at block 384 the previously stored event is discarded and the notified event from block 376 is stored as the new previously stored event with its angle designated "$\theta_1$". The process then continues at block 372.

Applying the process 370 to the FIGS. 15-17 while initially analyzing the angle which is complementary to θ, upon detecting the peak 360 with the event detector module 278, the event identifier module 282 queries the origin detector module 280 which determines that the angle which is complementary to θ at the time of the event is approximately −90° (see FIG. 16). The value of the angle which is complementary to θ of the peak 360 and time of the peak 360 are stored for this example.

Upon detecting the peak 362 with the event detector module 278, the event identifier module 282 queries the origin detector module 280 which determines that the angle which is complementary to θ at the time of the event is approximately 78° (see FIG. 16). This results in a difference with the stored value of the angle which is complementary to θ of the peak 360 which is greater than the 90°+/−20° range. Accordingly, the value of the angle which is complementary to θ of the peak 360 and time of the peak 360 are discarded and the value of the angle which is complementary to θ of the peak 362 and time of the peak 362 is stored.

Upon detecting the peak 364 with the event detector module 278, the event identifier module 282 queries the origin detector module 280 which determines that the angle which is complementary to θ at the time of the event is −82°. This results in a difference with the stored value of the angle which is complementary to θ of the peak 362 which is greater than the 90°+/−20° range. Accordingly, the value of the angle which is complementary to θ of the peak 362 and time of the peak 362 are discarded and the value of the angle which is complementary to θ of the peak 364 and time of the peak 364 is stored.

Upon detecting the peak 366 with the event detector module 278, the event identifier module 282 queries the origin detector module 280 which determines that the angle which is complementary to θ at the time of the event is 1°. This results in a difference with the stored value of the angle which is complementary to θ of the peak 364 which is within than the 90°+/−20° range. Accordingly, the value of the angle which is complementary to θ of the peak 364 and time of the peak 364 are associated with an AO event while the angle which is complementary to θ of the peak 366 and time of the peak 366 are associated with an MFA event.

Using the angle θ rather than the angle complementary to θ provides the same results since the first three peaks have values of about −1°, 12°, and −7° while the peak 366 has a value of about 90°. Accordingly, only the values associated with the peaks 364 and 366 have a sum in the range of 90°+/−20°.

The described system in different embodiments thus incorporates polar and spherical coordinates. The system automatically associates peaks in filtered SCG data within a polar or spherical coordinate system with, e.g., an AO event and/or an MFA event. The peak or peaks is/are associated with maxima in SCG data to identify the AO event and/or the MFA event in the SCG data to provide a reference point for a cardiac cycle segment. This allows the wearable health device 100 to autonomously (i.e., automatically) segment SCG data obtained with the wearable health device 100 into cardiac cycle segments.

The system and method described above automatically reduces intra-subject variability of SCG data which occurs when a single subject performs multiple SCG measurements with frequent manual attachment and detachment of the sensor setup. The SCG data in this scenario is adversely affected by placement errors of the sensor setup (position and orientation of the setup will not be the same each time).

The disclosed automatic system and method further reduces inter-subject variability of SCG data which occurs when SCG data is acquired across multiple subjects. In this scenario the SCG data has a high variability due to anatomical differences between subjects as well as difference in placement on the various subjects.

The disclosed embodiments are thus useful for many different use-cases. Examples include long term monitoring of hypertonia patients, sleep monitoring, and monitoring of subjects with cardiovascular diseases. In addition comparisons between different subjects are improved and automated evaluation systems can be used.

The disclosed embodiments thus provide SCG data which can be easily and automatically obtained while increasing the precision in comparison between data collections. The SCG data can be obtained without the need for expensive procedures.

Moreover, the SCG data can be obtained without a subject ever going to a health provider. A wearable health device with or without a gravity sensor in the sensor assembly can be purchased at, e.g., a local pharmacy or otherwise delivered to a subject. The device is then positioned by the subject or an individual on the subject's chest. The wearable health device then optionally ascertains the gravity axis as described above, and stores that data along with the acceleration data. At the end of the prescribed data collection duration, the wearable health device is removed and sent to a remote facility where the desired remaining steps of the method of FIG. 8 are performed.

While the disclosure has been described with reference to various embodiments, it will be understood that these embodiments are illustrative and that the scope of the disclosure is not limited to them. Many variations, modifications, additions, and improvements are possible. More generally, embodiments in accordance with the patent have been described in the context or particular embodiments.

Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A wearable health device system comprising:

a housing configured to be worn by a subject;

a sensor assembly supported by the housing and including a first accelerometer configured to sense acceleration along a first axis, and a second accelerometer configured to sense acceleration along a second axis which is not parallel to the first axis;

a memory including program instructions stored therein; and a processor operably connected to the sensor assembly and the memory, the processor configured to execute the program instructions to obtain seismocardiography (SCG) template data from the first and the second accelerometer, convert the SCG template data into one of a polar coordinate SCG template data and a spherical coordinate SCG template data, automatically identify at least one reference cardiac event in the obtained SCG data using the converted SCG data, and divide the obtained SCG data into at least one cardiac cycle segment based upon the referenced cardiac event.

2. The wearable health device system of claim 1, wherein the processor is configured to execute the program instructions to identify the at least one reference cardiac event in the obtained SCG template data using the converted SCG template data by:

identifying a first radial amplitude in the converted SCG template data;

comparing the first radial amplitude to a threshold amplitude; and determining that a first cardiac event has occurred based upon the comparing of the first radial amplitude to the threshold amplitude.

3. The wearable health device system of claim 2, wherein:

the processor is configured to execute the program instructions to convert the SCG template data into the spherical coordinate SCG data including the first radial amplitude, a first polar angle ($\theta_1$) between the first radial amplitude and a z-axis wherein the z-axis extends through the subject when the housing is worn by the subject, and a first azimuthal angle ($\varphi_1$) between the first radial amplitude and an x-axis; and identifying the at least one reference cardiac event in the obtained SCG template data using the converted SCG data includes identifying the first cardiac event as an aortic valve opening (AO) event when $-20° \leq \varphi_1 \leq 20°$ and $70° \leq \theta_1 \leq 110°$.

4. The wearable health device system of claim 3, wherein:

the processor is further configured to execute the program instructions to identify the at least one reference cardiac event in the obtained SCG data using the converted SCG data by determining that a second cardiac event has occurred based upon comparing a second radial amplitude to the threshold amplitude;

the processor is configured to execute the program instructions to convert the SCG data into the spherical SCG data including the second radial amplitude, a second polar angle ($\theta_2$) between the second radial amplitude and the z-axis, and a second azimuthal angle ($\varphi_2$) between the second radial amplitude and the x-axis; and identifying the at least one reference cardiac event in the obtained SCG data using the converted SCG data includes identifying the second cardiac event as a maximum force aorta (MFA) event when $-20° \leq \varphi_2 \leq 20°$ and $-20° \leq \theta_2 \leq 20°$.

5. The wearable health device system of claim 4, wherein the processor is further configured to execute the program instructions to identify the at least one reference cardiac event in the obtained SCG data using the converted SCG data by:

comparing the $\varphi_1$ with the $\varphi_2$; and identifying the first cardiac event as an AO event and the second cardiac event as an MFA event when $\varphi_1 + \varphi_2 = 90° \pm 20°$.

6. The wearable health device system of claim 5, wherein the processor is further configured to execute the program instructions to identify the at least one reference cardiac event in the obtained SCG data using the converted SCG template data by:

determining a difference in time between detection of the first radial amplitude and detection of the second radial amplitude;

comparing the difference in time to a time limit; and identifying the at least one reference cardiac event when the difference of time is within the time limit.

7. The wearable health device system of claim 2, wherein:

the processor is configured to execute the program instructions to convert the SCG data into the polar coordinate SCG data including the first radial amplitude, and a first angle based upon a polar angle between the first radial amplitude and a z-axis;

the processor is configured to execute the program instructions to convert the SCG data into the polar coordinate SCG data including a second radial amplitude, and a second angle based upon a polar angle between the second radial amplitude and the z-axis;

the z-axis extends through the subject when the housing is worn by the subject; and identifying the at least one reference cardiac event in the obtained SCG template data using the converted SCG template data includes determining that $70° \leq (\text{First angle} - \text{Second angle}) \leq 110°$.

8. The wearable health device system of claim 7, wherein:

the processor is further configured to execute the program instructions to identify the at least one reference cardiac event in the obtained SCG template data using the converted SCG template data by determining that a second cardiac event has occurred based upon comparing the second radial amplitude to the threshold amplitude; and the second radial amplitude immediately follows the first radial amplitude in the converted SCG template data.

9. The wearable health device system of claim 8, further comprising:

at least one filter, wherein the obtained SCG template data is filtered by the at least one filter prior to conversion to the polar coordinate SCG template data.

10. A method of referencing seismocardiography (SCG) data obtained by a wearable health device system comprising:

positioning a wearable health device on a chest of a subject;

obtaining SCG template data from a first and a second accelerometer of a sensor assembly supported by a housing of the wearable health device by executing with a processor program instructions stored in a memory, wherein the first accelerometer is configured to sense acceleration along a first axis, and the second accelerometer is configured to sense acceleration along a second axis which is not parallel to the first axis;

converting with the processor the SCG template data into one of a polar coordinate SCG template data and a spherical coordinate SCG template data;

automatically identifying with the processor at least one reference cardiac event in the obtained SCG template data using the converted SCG template data; and dividing the obtained SCG template data into at least one cardiac cycle segment based upon the referenced cardiac event.

11. The method of claim 10, wherein identifying with the processor at least one reference cardiac event in the obtained SCG template data using the converted SCG template data comprises:

identifying with the processor a first radial amplitude in the converted SCG template data;

comparing with the processor the first radial amplitude to a threshold amplitude; and determining with the processor that a first cardiac event has occurred based upon the comparing of the first radial amplitude to the threshold amplitude.

12. The method of claim 11, wherein:

converting with the processor the SCG template data into one of a polar coordinate SCG template data and a spherical coordinate SCG template data comprises converting the SCG template data into the spherical coordinate SCG template data including the first radial amplitude, a first polar angle ($\theta_1$) between the first radial amplitude and a z-axis wherein the z-axis extends through the subject when the housing is worn by the subject, and a first azimuthal angle ($\varphi_1$) between the first radial amplitude and an x-axis; and identifying with the processor at least one reference cardiac event in the obtained SCG template data using the converted SCG template data includes identifying the first cardiac event as an aortic valve opening (AO) event when $-20° \leq \varphi_1 \leq 20°$ and $70° \leq \theta_1 \leq 110°$.

13. The method of claim 12, wherein:

identifying with the processor at least one reference cardiac event in the obtained SCG template data using the converted SCG template data includes determining that a second cardiac event has occurred based upon comparing a second radial amplitude to the threshold amplitude;

converting the SCG template data into the spherical coordinate SCG template data includes converting the SCG template data into the spherical coordinate SCG template data including the second radial amplitude, a second polar angle ($\theta_2$) between the second radial amplitude and the z-axis, and a second azimuthal angle ($\varphi_2$) between the second radial amplitude and the x-axis; and identifying with the processor the at least one reference cardiac event in the obtained SCG template data using the converted SCG template data includes identifying the second cardiac event as a maximum force aorta (MFA) event when $-20° \leq \varphi_2 \leq 20°$ and $-20° \leq \theta_2 \leq 20°$.

14. The method of claim 13, wherein identifying with the processor at least one reference cardiac event in the obtained SCG template data using the converted SCG template data further comprises:

comparing with the processor the $\varphi_1$ with the $\varphi_2$; and identifying with the processor the first cardiac event as an AO event and the second cardiac event as an MFA event when $\varphi_1 + \varphi_2 = 90° \pm 20°$.

15. The method of claim 14, wherein identifying with the processor at least one reference cardiac event in the obtained SCG template data using the converted SCG template data further comprises:

determining with the processor a difference in time between detection of the first radial amplitude and detection of the second radial amplitude;

comparing with the processor the difference in time to a time limit stored in the memory; and identifying with the processor the at least one reference cardiac event when the difference of time is within the time limit.

16. The method of claim 11, wherein:

converting with the processor the SCG template data into one of a polar coordinate SCG template data and a spherical coordinate SCG template data includes converting the SCG template data into the polar coordinate SCG template data including the first radial amplitude, and a first angle based upon a polar angle between the first radial amplitude and a z-axis;

converting with the processor the SCG template data into one of a polar coordinate SCG template data and a spherical coordinate SCG template data includes converting the SCG template data into the polar coordinate SCG template data including a second radial amplitude, and a second angle based upon a polar angle between the second radial amplitude and the z-axis;

the z-axis extends through the subject when the housing is worn by the subject; and identifying with the processor at least one reference cardiac event in the obtained SCG template data using the converted SCG template data includes determining that $70° \leq (\text{First angle} - \text{Second angle}) \leq 110°$.

17. The method of claim 16, wherein:

identifying with the processor at least one reference cardiac event in the obtained SCG template data using the converted SCG template data includes determining that a second cardiac event has occurred based upon comparing the second radial amplitude to the threshold amplitude; and the second radial amplitude immediately follows the first radial amplitude in the converted SCG template data.

18. The method of claim 17, further comprising:

filtering the obtained SCG template data with at least one filter prior to converting with the processor the SCG template data into the polar coordinate SCG template data.

* * * * *